United States Patent [19]

McEachern

[11] Patent Number: 4,563,275

[45] Date of Patent: Jan. 7, 1986

[54] CHROMATOGRAPHY COLUMN AND END PLUG ASSEMBLY

[75] Inventor: Dan L. McEachern, Alameda, Calif.

[73] Assignee: Bio-Rad Laboratories, Inc., Richmond, Calif.

[21] Appl. No.: 636,512

[22] Filed: Aug. 1, 1984

[51] Int. Cl.[4] ............................................. B01D 15/08
[52] U.S. Cl. ..................................... 210/198.2; 55/386
[58] Field of Search ......................... 210/198.2; 55/386

[56] References Cited

U.S. PATENT DOCUMENTS

| | | | |
|---|---|---|---|
| 3,395,441 | 8/1968 | Herbenar | 29/441 |
| 4,083,702 | 4/1978 | Hartigan et al. | 55/386 |
| 4,283,280 | 8/1981 | Brownlee | |
| 4,389,313 | 6/1983 | Charney et al. | 210/198.2 |
| 4,451,363 | 5/1984 | Brownlee et al. | 210/198 |
| 4,451,364 | 5/1984 | Higgins et al. | 210/198.2 |
| 4,451,365 | 5/1984 | Sattler | 55/386 |

Primary Examiner—John Adee
Attorney, Agent, or Firm—Townsend and Townsend

[57] ABSTRACT

A novel column cartridge for a chromatography apparatus, particularly HPLC, is comprised of a hollow metal tube, open at both ends and having internal shoulders facing each open end, and a pair of end plugs each having a frusto-conical shape at its outer end. The end plugs are sealed into place by rolling the tube end to compress it against the frustum surface, leaving a short length of plug extending beyond the tube end for compression sealing against a conventional holder or mounting device.

6 Claims, 4 Drawing Figures

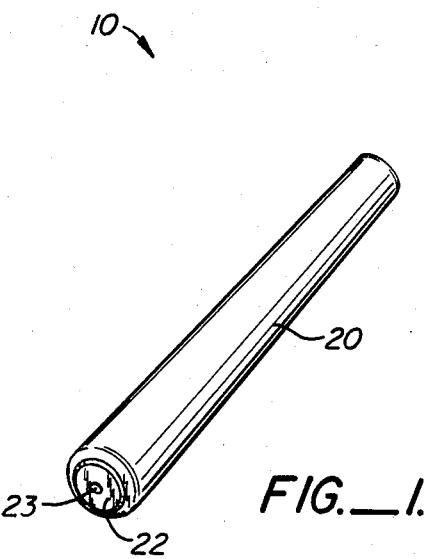
FIG._1.
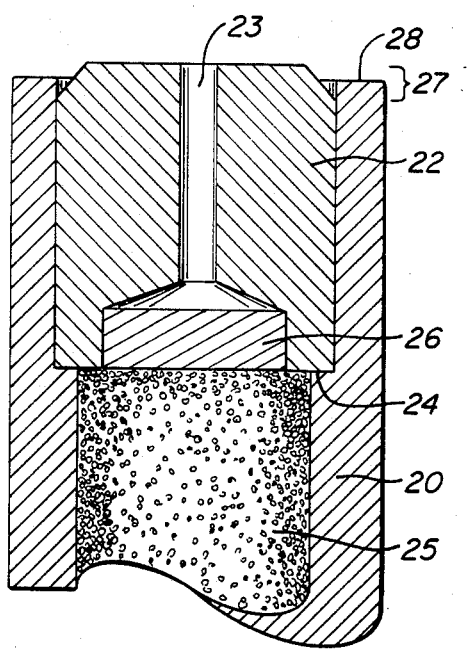
FIG._2.
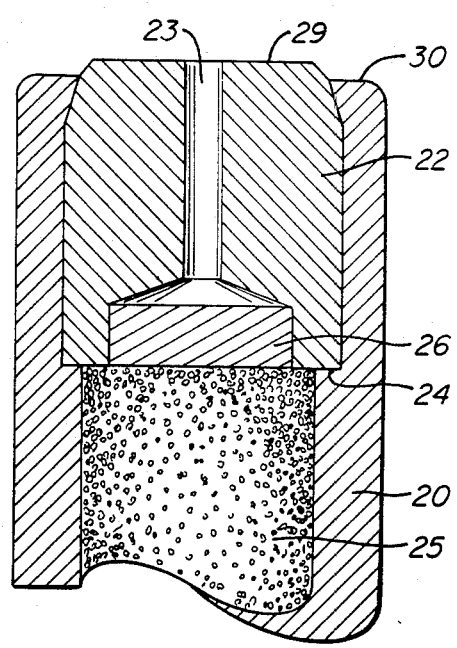
FIG._3.

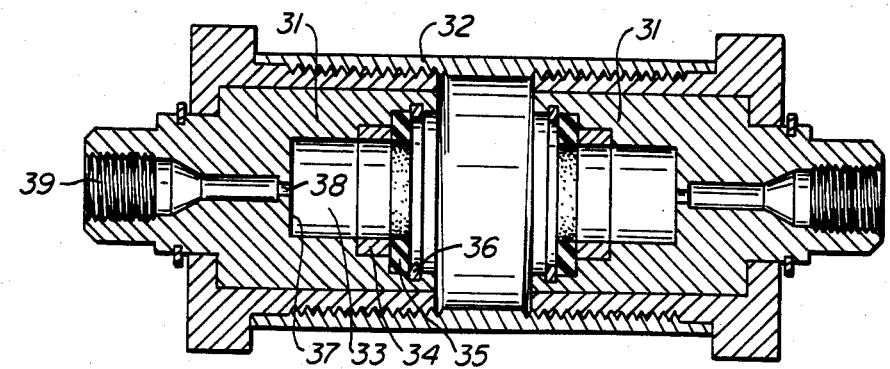
FIG._4.

CHROMATOGRAPHY COLUMN AND END PLUG ASSEMBLY

BACKGROUND OF THE INVENTION

1. Field of the Invention

This invention relates to column chromatography. In particular this invention relates to the structure of chromatography columns and methods for sealing the ends of such columns in specifically designed holder assemblies to provide leak-proof connection to high pressure fluid lines.

2. Description of the Prior Art

Chromatography in general and high pressure liquid chromatography (HPLC) in particular are widely used for analytical and preparative separations of mixtures of chemical species. For optimum accuracy and efficiency as well as safe operation, the sealing of the separation column into the remainder of the apparatus is a serious concern. This concern is particularly acute in HPLC due to the high pressures involved, which generally range from about 1,000 to about 10,000 psi.

The seal which is most frequently connected and disconnected by the user is that between the column and the tubing which connects it to the rest of the apparatus (which includes a high pressure pump, liquid transfer lines, etc.). The user frequently removes and replaces the column from one separation to the next in order to adapt the apparatus to accommodate a range of mixtures. This is generally accomplished by using a seal which is capable of being assembled and disassembled repeatedly by the user. The use of compression fittings with metal-to-metal contact is prevalent in the equipment currently available. Examples of such fittings are those manufactured by Crawford Fitting Company of Cleveland, Ohio (sold under the trademark "Swagelok") and a similar seal made by Parker-Hannifin, also of Cleveland, Ohio. The disadvantage of such fittings is that they are expensive and are usable only a limited number of times before their sealing capacity is lost and replacement is necessary. Furthermore, these fittings must be assembled with the use of tools, and require considerable manual dexterity on the part of the user to effect a connection to the chromatography system. Additionally, some columns and their packings exhibit short lifetimes and must be frequently replaced in order to obtain acceptable performance of the apparatus. Low cost, disposable column systems with reusable cartridge holders overcome the disadvantages and inconveniences of conventional HPLC columns and column fittings. Examples of HPLC cartridge systems are those manufactured by CHROMPACK of Bridgewater, N.J. and Brownlee Labs of Santa Clara, Calif.

SUMMARY OF THE INVENTION

A column cartridge of a novel and unusually simple design is provided herein. The column packing in this cartridge is secured against the end plugs without the use of a fitting, and the assembled cartridge is capable of a leak-proof compression-type seal at each end against a mating HPLC column holder or other type of mounting device in a manner which does not degrade in effectiveness upon repeated connecting and disconnecting. These effects are achieved through the use of end plugs which have a frusto-conical shape at one end, and a tube having shoulders on its internal surface to receive the end plugs, the shoulders being positioned such that when the plugs are in place, each open end of the tube lies between the two planes of the frustum. Preparation of the cartridge for use is completed by rolling the tube end, thereby compressing it against the frustum surface to secure the plug in place. A short length of plug is left extending beyond the tube end, permitting the compression sealing of the cartridge to the mounting surface of a holder or other mounting device.

BRIEF DESCRIPTION OF THE DRAWINGS

FIG. 1 is a perspective view of an illustrative cartridge according to the present invention, with end plugs sealed into place;

FIG. 2 is a side cutaway view of one end of the cartridge of FIG. 1, showing the end plug in place before the end of the tube is sealed around it; and FIG. 3 is the same view as FIG. 1, except that it shows the cartridge after sealing.

FIG. 4 is a side cutaway view of a holder suitable for use with the cartridge of FIGS. 1, 2 and 3.

DESCRIPTION OF THE SPECIFIC AND PREFERRED EMBODIMENTS

Referring to FIG. 1, an exemplary chromatographic column cartridge 10 is shown. The cartridge contains a hollow cylindrical tube 20 for containing a conventional packing material for use as a solid phase separation medium in a chromatographic separation. The tube is fabricated of rigid but formable metal for reasons which will become apparent in the discussions of FIGS. 2 and 3 below. The particular metal used is not critical, although preferably inert to both the column packing and the mobile phase used in the separation process. Conventional HPLC column materials may be used, notably 316 Stainless Steel.

The tube 20 terminates at each end with sealing plugs 21 and 22, each of which has an orifice 23 to permit passage of the sample components and the carrier fluid comprising the mobile phase. The plug is fabricated of a resilient sealing-type material, such as that used in conventional gaskets. Again, it is preferred that the plug be inert to all materials in contact with it. Fluoropolymers, such as TFE, are particularly useful as plug materials. The tube 20 is curved inward over the plug at each end leaving a small portion of plug protruding beyond the end of the tubing.

Turning to FIG. 2, it is seen that the interior of the tube 20 has a circular shoulder 24 extending around the circumference of the inner tube surface and coplanar with the end of the column bed 25. The embodiment shown in the figure further illustrates a preferred construction whereby the orifice 23 is a through passage which is widened at the inner end of the plug to accommodate a filter or retaining means 26. The latter is a unit conventionally used in HPLC columns to support and retain the column packing and to help distribute the flow of the mobile phase over the cross-sectional area of the tube passage.

The plug 22 has a terminal portion shaped to form a frustum 27. The figure shows the components immediately after the plug has been placed inside the tube, prior to sealing. The dimensions of the components are selected such that the tube rim 28 is located at a level which is approximately in the middle of the frustum.

Once the plug is in place, sealing is accomplished by the use of a rolling tool designed to deform the end of the tube a specified amount, causing it to curve inward uniformly around the circumference of the tube. This compresses the tube against the plug and also deforms the plug to some extent as shown in FIG. 3. As is apparent from the figure, the conical shape of the end plug permits the rolled tube end to lock the plug tightly in place against the shoulder 24.

Once the tube end has been rolled, the exposed plug end 29 extends beyond the end of the rolled tubing 30, so that the plug will form a seal when the cartridge is axially compressed between the opposing surfaces of a mounting device. One example of such a device is shown in FIG. 4, which essentially consists of a pair of end cap nuts 31 threaded into a common sleeve 32. The column shown in FIGS. 1 through 3 fits snugly into the interior space 33 of the holder where it is sealed laterally by a high pressure ball seal 34, a washer 35 and snap ring 36. At each end of the column, the exposed plug end (29 in FIG. 3) is seated against a flat surface 37, with the orifice (23 in FIG. 3) in communication with a passageway 38 of equal diameter. The latter expands outward to a threaded portion 39 to which a standard tube fitting can be connected.

A further example of such a device is the holder shown in FIGS. 1 and 2 of Brownlee, U.S. Pat. No. 4,283,280 (Aug. 11, 1981), incorporated herein by reference. In general, the holder provides a fluid-tight means for connecting the cartridge to fluid flow lines in an HPLC apparatus.

Despite its simplicity of construction, the assembly of the present invention is unusually effective in sealing when mounted in a holder and tightened down, since the pressure exerted by the holder on the protruding end of the end plug causes the internal portion of the plug to expand. This expansion increases the sealing effect of the plug against the shoulder as well as the inner surface of the rolled portion of the tube.

The foregoing description is offered for illustrative purposes only. Numerous modifications and variations, still falling within the spirit and scope of the invention as claimed herein below, will be readily apparent to those skilled in the art.

What is claimed is:

1. A chromatographic column cartridge comprising:
   a cylindrical tube of formable metal having open ends and a pair of shoulders extending around the internal circumference thereof, one shoulder facing each said end; and
   a pair of resilient seal plugs shaped to fit inside said tube ends and to rest on said shoulders, each said plug containing a longitudinal passage communicating the exposed end surface thereof with the interior of said tube, the outer terminal portion of each said plug having the form of a frustum tapering outward, extending across and terminating beyond said tube end.

2. A cartridge according to claim 1 in which the inner end of said longitudinal passage is widened to accommodate a filter capable of passing a mobile phase while retaining chromatographic packing material in said tube.

3. A cartridge according to claim 1 in which said plugs are formed of a fluorocarbon polymer and said tube is formed of stainless steel.

4. A chromatographic column cartridge comprising:
   a rigid cylindrical tube having open ends and a pair of shoulders extending around the internal circumference thereof, one shoulder facing each said end, and each said end curving inward whereby the diameter of the opening at each end is less than the internal diameter of the portion of said tube between said shoulder and said end; and
   a pair of resilient seal plugs, one said plug retained at each end of said tube in the space between said shoulder and said opening, each said plug fitting snugly within said space and terminating at its outer end in a frustum tapering outward and protruding through said opening.

5. A cartridge according to claim 4 in which the inner end of said longitudinal passage is widened to accommodate a filter capable of passing a mobile phase while retaining chromatographic packing material in said tube.

6. A cartridge according to claim 4 in which said plugs are formed of a fluorocarbon polymer and said tube is formed of stainless steel.

* * * * *